US007850616B1

(12) United States Patent
Gill et al.

(10) Patent No.: US 7,850,616 B1
(45) Date of Patent: Dec. 14, 2010

(54) DETERMINATION OF DIASTOLIC HEART FAILURE

(75) Inventors: Jong Gill, Valencia, CA (US); Xiaoyi Min, Thousand Oaks, CA (US); Gene A. Bornzin, Simi Valley, CA (US); Falkenberg Eric, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 892 days.

(21) Appl. No.: 11/154,064

(22) Filed: Jun. 15, 2005

(51) Int. Cl.
*A61B 5/021* (2006.01)
*A61B 5/0225* (2006.01)
(52) U.S. Cl. .................. 600/526; 600/485; 600/486
(58) Field of Classification Search ............... 600/485, 600/486, 526; 607/23
See application file for complete search history.

(56) References Cited

U.S. PATENT DOCUMENTS

| | | | |
|---|---|---|---|
| 4,712,555 A | 12/1987 | Thornander et al. | 128/419 PG |
| 4,730,619 A * | 3/1988 | Koning et al. | 607/23 |
| 4,788,980 A | 12/1988 | Mann et al. | 128/419 PG |
| 4,940,052 A | 7/1990 | Mann et al. | 128/419 PG |
| 4,944,298 A | 7/1990 | Sholder | 128/419 PG |
| 5,466,254 A | 11/1995 | Helland | 607/123 |
| 5,476,483 A | 12/1995 | Bornzin et al. | 607/17 |
| 6,314,323 B1 | 11/2001 | Ekwall | 607/23 |
| 6,328,699 B1 | 12/2001 | Eigler et al. | 600/486 |
| 6,561,986 B2 * | 5/2003 | Baura et al. | 600/526 |
| 6,643,548 B1 | 11/2003 | Mai et al. | |
| 7,010,347 B2 * | 3/2006 | Schecter | 607/17 |
| 7,192,399 B2 * | 3/2007 | Kjellstrom et al. | 600/485 |
| 2003/0055344 A1 | 3/2003 | Eigler et al. | 600/486 |
| 2003/0055345 A1 | 3/2003 | Eigler et al. | 600/486 |
| 2003/0100925 A1 | 5/2003 | Pape et al. | |
| 2003/0153837 A1* | 8/2003 | McIntyre | 600/485 |
| 2004/0254483 A1* | 12/2004 | Zdeblick et al. | 600/486 |

FOREIGN PATENT DOCUMENTS

WO   WO 01/51123 A1   7/2001

OTHER PUBLICATIONS

Berne, Robert M. et al., Cardiovascular Physiology, Sixth Edition, 1 page, page number unknown.
Barbier, Paolo MD et al., "*Left Atrial Relaxation and Left Ventricular Systolic Function Determine Left Atrial Reservoir Function,*" Circulation. 1999;100:427-436.
Gibson, Derek G. et al., "*Clinical Assessment of Left Ventricular Diastolic Function,*" Heart 2003;89:231-238.
Hofmann, Thomas MD et al., "*Simultaneous Measurement of Pulmonary Venous Flow by Intravascular Catheter Doppler Velocity and Transesophageal Doppler Echocardiography: Relation to Left Atrial Pressure and Left Atrial and Left Ventricular Function,*" J Am Coll Cardiol 1995;26:239-49.
Rivas-Gotz, Carlos MD et al., "*Time Interval Between Onset of Mitral Inflow and Onset of Early Diastolic Velocity by Tissue Doppler: A Novel Index of Left Ventricular Relaxation,*" J Am Coll Cardiol, vol. 42, No. 8 (2003), pp. 1463-1470.

(Continued)

*Primary Examiner*—Carl H. Layno
*Assistant Examiner*—Tammie K Heller

(57) ABSTRACT

An exemplary method includes detecting a change in state of a cardiac valve, detecting elongation of the left ventricle substantially along its major axis, determining a time difference between the change in state of the cardiac valve and the elongation of the left ventricle and, based at least in part on the time difference, deciding whether a diastolic abnormality exists. Other exemplary methods, devices, systems, etc., are also disclosed.

6 Claims, 12 Drawing Sheets

OTHER PUBLICATIONS

Kawaguchi, Miho MD et al., "*Combined Ventricular Systolic and Arterial Stiffening in Patients With Heart Failure and Preserved Ejection Fraction—Implications for Systolic and Diastolic Reserve Limitations,*" Circulation. 2003;107:714-720.I.

Shioi, Tetsuo MD et al., "*Rapamycin Attenuates Load-Induced Cardiac Hypertrophy in Mice,*" Circulation. 2003;107:1664-1670.

Tanner, Hildegard et al., "*The Prevalence of Anemia in Chronic Heart Failure,*" International Journal of Cardiology 86 (2002):115-121.

* cited by examiner

DETERMINATION OF DIASTOLIC HEART FAILURE

TECHNICAL FIELD

Subject matter presented herein generally relates to determination of diastolic heart failure. Various exemplary methods, devices, systems, etc., concern use of an implantable cardiac therapy device to aid in determination of diastolic heart failure.

BACKGROUND

Gibson and Francis recently reported that "diastolic left ventricular disease is being increasingly incriminated as a cause of limitation of exercise tolerance, whether or not ejection fraction is normal, though the mechanisms by which it does so are far from clear" and that "it has been suggested that no diastolic abnormality at all need be demonstrated for a diagnosis of possible or probable diastolic heart failure to be made" ("Clinical Assessment of Left Ventricular Diastolic Function," *Heart* 2003; 89:231-238).

As noted by Gibson and Francis, left ventricular diastole involves both muscle mechanics and fluid mechanics. Such mechanisms may include decline of the myocardial active state following systole, passive effects of connective tissue (compression or extension of connective tissue may store potential energy from systole and release it in early diastole and, in late diastole, properties of connective tissue may determine ventricular compliance), rapid changes in atrial and ventricular pressures, transmitral flow, interactions from right ventricle and pericardium, and atrial systole. Further, such mechanisms may be interrelated, for example, a fluid pressure may facilitate muscle contraction.

In a clinical setting, a care provider may measure many parameters in an effort to determine whether a patient suffers from diastolic heart failure whereas a typical implantable device lacks resources to perform adequate measurements and make robust determinations. Consequently, a need exists for measurement and determination techniques that can allow an implantable device to diagnose diastolic left ventricular disease.

As described herein, various techniques rely on parameters that relate to muscle mechanics and/or fluid mechanics to detect conditions that may be associated with diastolic heart failure.

SUMMARY

An exemplary method includes detecting a change in state of a cardiac valve, detecting elongation of the left ventricle substantially along its major axis, determining a time difference between the change in state of the cardiac valve and the elongation of the left ventricle and, based at least in part on the time difference, deciding whether a diastolic abnormality exists. Other exemplary methods, devices, systems, etc., are also disclosed.

In general, the various methods, devices, systems, etc., described herein, and equivalents thereof, are optionally suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Exemplary Stimulation Device

The techniques described below are optionally implemented in connection with any stimulation device that is configured or configurable to stimulate and/or shock tissue.

Figure 1:
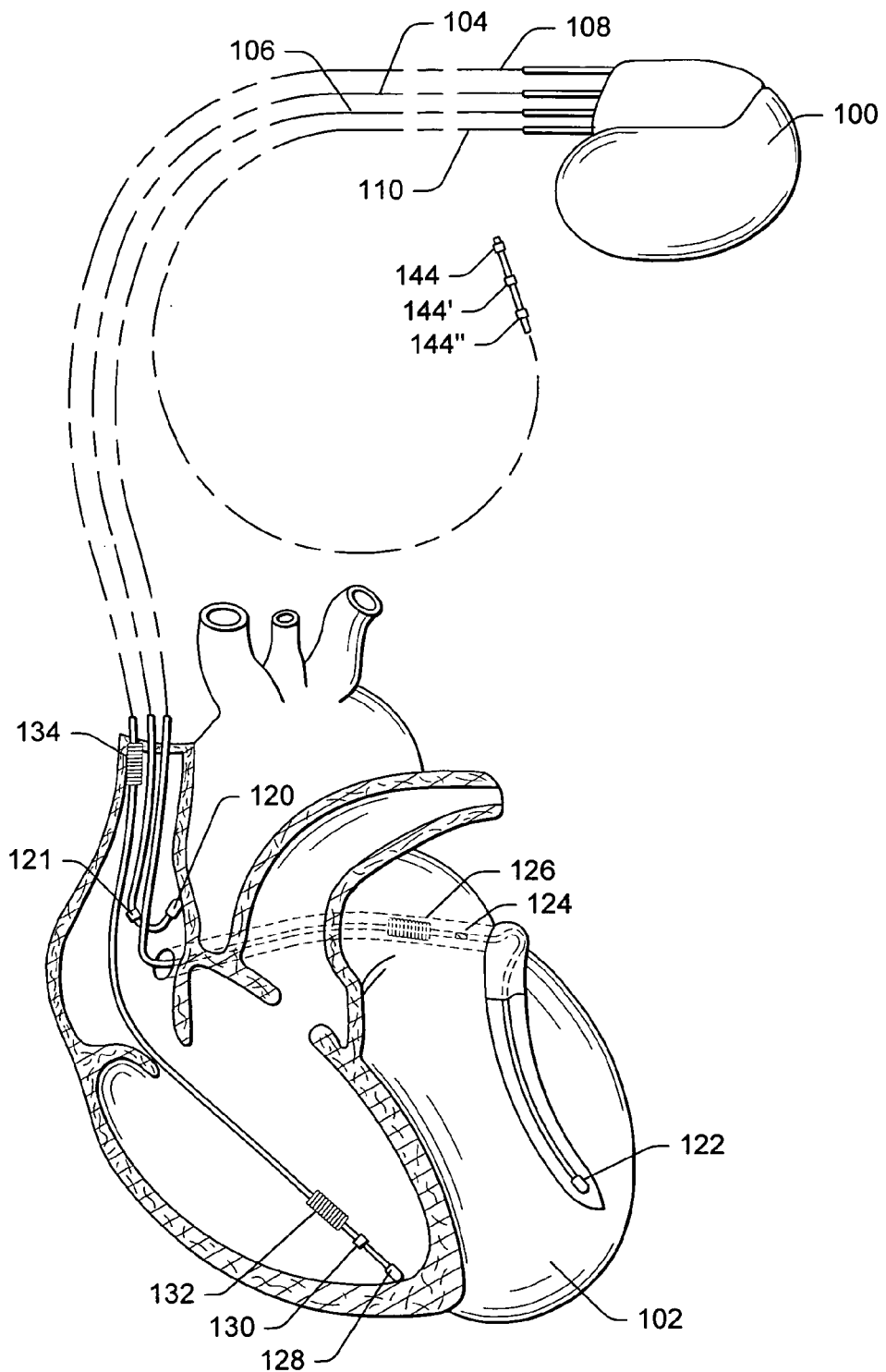
FIG. 1 is a simplified diagram illustrating an exemplary implantable stimulation device in electrical communication with at least three leads implanted into a patient's heart and at least one other lead for delivering stimulation and/or shock therapy.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves, non-myocardial tissue, other nerves, etc. In addition, the device 100 includes a fourth lead 110 having, in this implementation, three electrodes 144, 144', 144" suitable for stimulation of autonomic nerves, non-myocardial tissue, other nerves, etc. For example, this lead may be positioned in and/or near a patient's heart or near an autonomic nerve within a patient's body and remote from the heart. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves, non-myocardial tissue, other nerves, etc.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, non-myocardial tissue, other nerves, etc., wherein such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, non-myocardial tissue, other nerves, etc., wherein such an electrode may be positioned on the lead or a bifurcation or leg of the lead.

Figure 2:
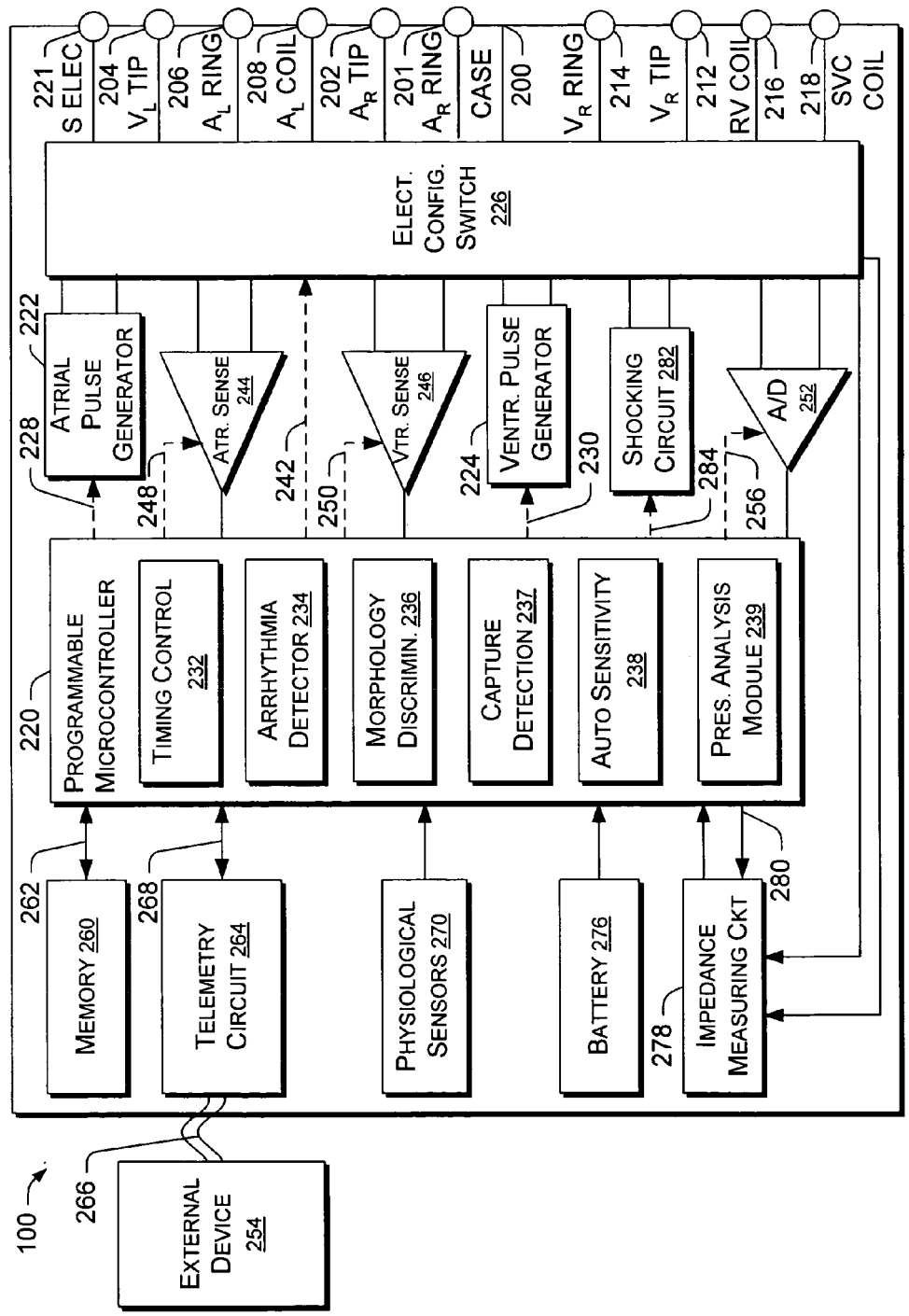
FIG. 2 is a functional block diagram of an exemplary implantable stimulation device illustrating basic elements that are configured to provide cardioversion, defibrillation, pacing stimulation and/or other tissue and/or nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves, non-myocardial tissue, other nerves, etc. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, autonomic nerve stimulation, non-myocardial tissue stimulation, other nerve stimulation, etc.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing and/or pacing, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing and/or shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

To support right chamber sensing, pacing, and/or shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology discrimination module 236, a capture detection module 237, a auto sensitivity module 238, a pressure analysis module 239 and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

The pressure analysis module 239 may perform a variety of tasks related to, for example, left atrial pressure, left ventricular pressure, aortic pressure, right atrial pressure, right ventricular pressure, etc. This component can be utilized by the stimulation device 100 in determining therapy in response to pressure, a derivative thereof, and/or other parameter. The pressure analysis module 239 may be implemented in hardware as part of the microcontroller 220, or as software/firmware instructions programmed into the device and executed on the microcontroller 220 during certain modes of operation. The pressure analysis module 239 may optionally implement various exemplary methods described herein. The pressure analysis module 239 may interact with the capture physiological sensors 270, the impedance measuring circuit 278 and optionally other modules.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (ND) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve or other tissue stimulation lead 110 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation," to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses.

Pressure sensors for sensing left atrial pressure are discussed in U.S. Patent Application US2003/0055345 A1, to Eigler et al., which is incorporated by reference herein. The discussion pertains to a pressure transducer permanently implantable within the left atrium of the patient's heart and operable to generate electrical signals indicative of fluid pressures within the patient's left atrium. According to Eigler et al., the pressure transducer is connected to a flexible electrical lead, which is connected in turn to electrical circuitry, which includes digital circuitry for processing electrical signals. Noted positions of the transducer include within the left atrium, within a pulmonary vein, within the left atrial appendage and in the septal wall.

The exemplary device 100 optionally includes a connector capable of connecting a lead that includes a pressure sensor. For example, the connector 221 optionally connects to a pressure sensor capable of receiving information pertaining to chamber pressures or other pressures. Pressure information is optionally processed or analyzed by the pressure analysis module 239.

A study by Hofmann et al., "Simultaneous measurement of pulmonary venous flow by intravascular catheter Doppler velocimetry and transesophageal Doppler echocardiography: relation to left atrial pressure and left atrial and left ventricular function," *J Am Coll Cardiol*. 1995 July; 26(1):239-49, used a "microtip" pressure transducer and noted that mean left atrial pressure was strongly correlated with the ratio of systolic to diastolic peak velocity, systolic velocity-time integral, time to maximal flow velocity and the ratio of systolic to diastolic flow duration. In particular, Hofmann et al. reported that the ratio of systolic to diastolic peak velocity and the time to maximal flow velocity were identified as strong independent predictors of mean left atrial pressure and that left atrial compliance was not found to be an independent predictor of mean left atrial pressure. This study indicates that surrogates may exist for indirect measurement or estimation of left atrial pressure or mean left atrial pressure.

Commercially available pressure transducers include those marketed by Millar Instruments (Houston, Tex.) under the mark MIKROTIP®. A study by Shioi et al., "Rapamycin Attenuates Load-Induced Cardiac Hypertrophy in Mice," *Circulation* 2003; 107:1664, measured left ventricular pressures in mice using a Millar pressure transducer inserted through the LV apex and secured in the LV apex with a purse-string suture using 5-0 silk. Various exemplary methods, devices, systems, etc., described herein optionally use such a pressure transducer to measure pressures in the body (e.g., chamber of heart, vessel, etc.).

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense pressure, respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device 100 optionally includes circuitry capable of sensing heart sounds and/or vibration associated with events that produce heart sounds. Such circuitry may include an accelerometer as conventionally used for patient position and/or activity determinations. Accelerometers typically include two or three sensors aligned along orthogonal axes. For example, a commercially available micro-electromechanical system (MEMS) marketed as the ADXL202 by Analog Devices, Inc. (Norwood, Mass.) has a mass of about 5 grams and a 14 lead CERPAK (approx. 10 mm by 10 mm by 5 mm or a volume of approx. 500 $mm^3$). The ADXL202 MEMS is a dual-axis accelerometer on a single monolithic integrated circuit and includes polysilicon springs that provide a resistance against acceleration forces. The term MEMS has been defined generally as a system or device having micro-circuitry on a tiny silicon chip into which some mechanical device such as a mirror or a sensor has been manufactured. The aforementioned ADXL202 MEMS includes micro-circuitry and a mechanical oscillator.

While an accelerometer may be included in the case of an implantable pulse generator device, alternatively, an accelerometer communicates with such a device via a lead or through electrical signals conducted by body tissue and/or fluid. In the latter instance, the accelerometer may be positioned to advantageously sense vibrations associated with cardiac events. For example, an epicardial accelerometer may have improved signal to noise for cardiac events compared to an accelerometer housed in a case of an implanted pulse generator device.

The stimulation device 100 additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264. Trigger IEGM storage also can be achieved by magnet.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds (HF indications—pulmonary edema and other factors); detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses in a range of joules, for example, conventionally up to about 40 J, as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

In low-energy cardioversion, an ICD device typically delivers a cardioversion stimulus (e.g., 0.1 J, etc.) synchronously with a QRS complex; thus, avoiding the vulnerable period of the T wave and avoiding an increased risk of initiation of VF. In general, if antitachycardia pacing or cardioversion fails to terminate a tachycardia, then, for example, after a programmed time interval or if the tachycardia accelerates, the ICD device initiates defibrillation therapy.

While an ICD device may reserve defibrillation as a latter tier therapy, it may use defibrillation as a first-tier therapy for VF. In general, an ICD device does not synchronize defibrillation therapy with any given portion of a ECG. Again, defibrillation therapy typically involves high-energy shocks (e.g., 5 J to 40 J), which can include monophasic or unidirectional and/or biphasic or bidirectional shock waveforms. Defibrillation may also include delivery of pulses over two current pathways.

Figure 3:
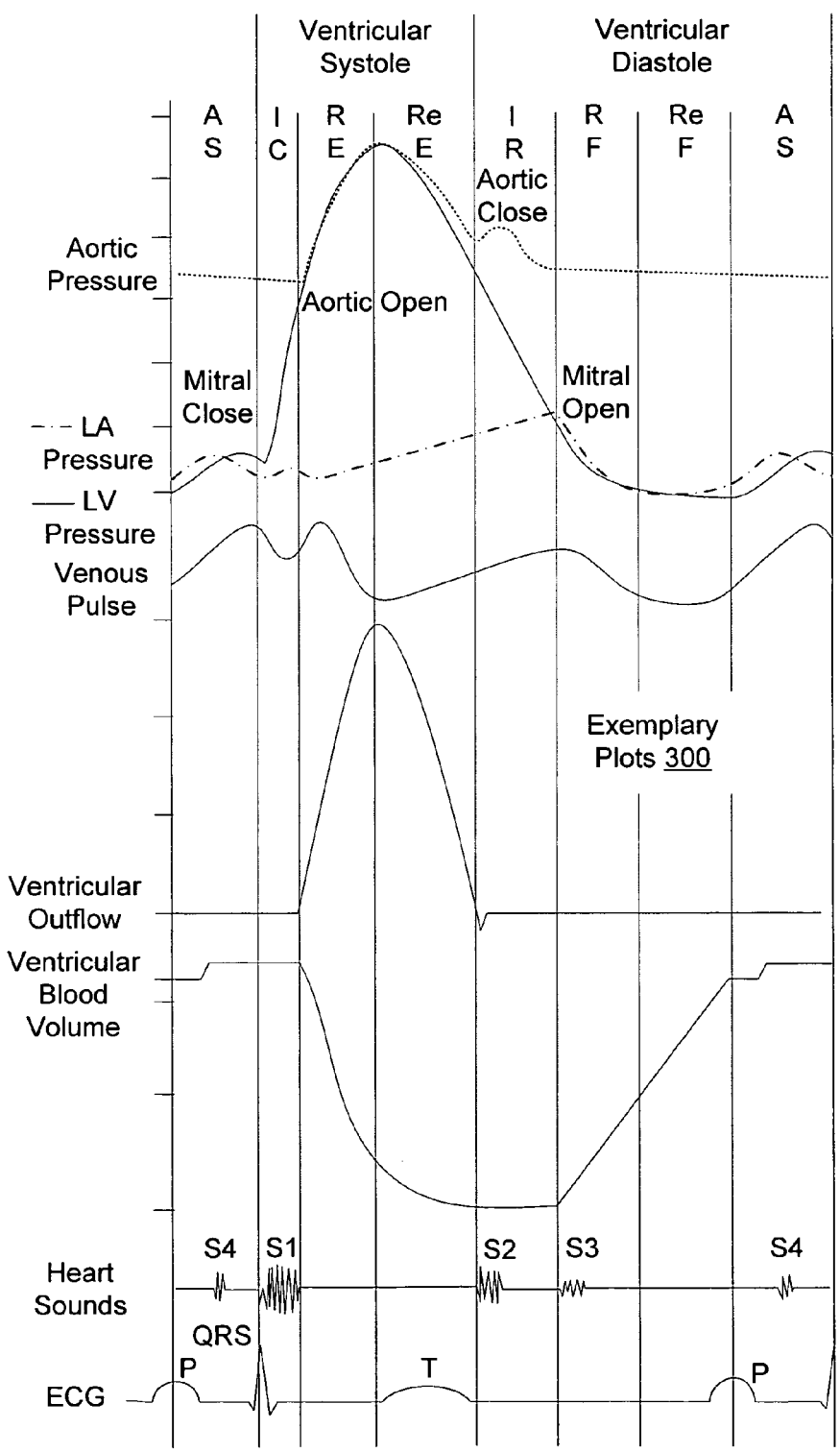
FIG. 3 is a diagram of various parameters and their variations during a cardiac cycle as typical of a Wigger diagram.

FIG. 3 shows a plot 300 of various parameters versus time during a cardiac cycle. The plot 300 is adapted from a Wigger diagram in an article entitled "Cardiovascular System Review" by Rogers and Humburg. The plot 300 shows various phases of the cardiac cycle including atrial systole (AS), isovolumic contraction (IS), rapid ejection (RE), reduced ejection (ReE), isovolumic relaxation (IR), rapid filling (RF), and reduced filling (ReF). In particular, the plot 300 illustrates how various parameters vary during ventricular systole and diastole. The parameters include aortic pressure, left atrial pressure, left ventricular pressure, venous pulse, ventricular outflow, ventricular volume, heart sounds, electrical activity (e.g., electrocardiogram) and valve dynamics. As described herein, various parameters are used to determine heart condition and to optionally adjust therapy.

A condition of particular interest is diastolic heart failure (DHF), which is generally defined to be a heart failure with ejection fraction (EF) greater than 50% (e.g., a "normal" ejection fraction). A relationship between left ventricular ejection fraction (LVEF) and heart failure typically exists where a decrease in LVEF corresponds to a progression or worsening of heart failure. A study by Moschovitis et al. "The prevalence of anemia in chronic heart failure," *Int J. Cardiol.* 202 November; 86(1):115-21, found an inverse relationship between NYHA class and LVEF with class I patients having an average ejection fraction of 45%, class II patients having an average LVEF of 32%, class III patients having an average LVEF of 25% and class IV patients having an average LVEF of 25%. Consequently, robust diagnosis of DHF should consider parameters other than EF.

Gibson and Francis, "Clinical Assessment of Left Ventricular Diastolic Function," *Heart* 2003; 89:231-238, mention a variety of parameters related to diastolic function. For example, a short isovolumic relaxation time (IVRT) may indicate a raised filling pressure, a poor prognosis and possibly conventional treatment with diuretics and ACE inhibitors and incoordinate relaxation may be a marker of diastolic disease. A normal range of IVRT is typically about 60 ms to about 90 ms.

Referring to the plot 300, isovolumic relaxation (IR) occurs during ventricular diastole and is demarcated approximately by closure of the aortic valve and second heart sound (S2) and approximately by opening of the mitral valve and third heart sound (S3), which is more prominent in children and those with abnormal ventricular function when compared to normal adults. In general, onset of IR is more well-defined in comparison to the end of IR. During IR, ventricular pressure decreases; however, the blood volume remains constant because the valves are closed. The volume of blood that remains in a ventricle is called the end-systolic volume and is typically about 50 ml for the left ventricle. According to the study by Gibson and Francis, onset of isovolumic relaxation time commences with aortic valve closure, which can be identified by the aortic component (A2) of the second heart sound (S2); however, the end is less well defined. Gibson and Francis note that in normal adults, the time interval from A2 to mitral cusp separation is about 60 ms and that to the onset of Doppler flow is approximately 85 ms. As described herein, S2 or A2 may be used to determine cardiac condition. For example, S2 or A2 may represent events from which time to a subsequent event is measured or S2 or A2 may be analyzed for characteristics that may indicate heart condition. Gibson and Francis also note that IVRT is not a measure of relaxation; however, a very short IVRT is a reliable sign of a raised atrial pressure and a prolonged IVRT indicates a combination of ventricular disease with normal or near normal filling pressure. Thus, as described further below, IVRT may act as an indicator of disease.

A fourth heart sound (S4) may be present in the late stage of diastole and associated with atrial contraction, or kick, where the final 20% of the atrial output is delivered to the ventricles. If the ventricle is stiff and non-compliant, as in ventricular hypertrophy due to long-standing hypertension, the pressure wave generated as the atria contract produces an fairly distinct S4.

Gibson and Francis identify incoordinate relaxation or incoordination as a major cause in prolonging IR as it occurs around the transition from IR and rapid ventricular filling (RF). Incoordinate relaxation, refers to changes in shape of the left ventricle during early diastole and may be assessed by comparing longitudinal motion along a major axis of the left ventricle to motion along a minor axis. In general, the major axis of the left ventricle may be defined by the apex of the left ventricle and the atrioventricular ring (AVR) or mitral annulus (MA). Studies have shown that the apex of the left ventricle remains relatively stationary while the mitral annulus has a significant displacement component along the axis. Thus, observation of the mitral annulus may provide useful information, for example, amplitude, velocity and/or timing information.

Various studies indicate that amplitude of the mitral annulus correlates with ejection fraction and that timing of onset of mitral annulus movement may be used in conjunction with a marker (e.g., preferably insensitive to changes in heart rate or loading conditions) to determine cardiac condition.

A study by Rivas-Gotz et al., "Time Interval Between Onset of Mitral Inflow and Onset of Early Diastolic Velocity by Tissue Doppler: A Novel Index of Left Ventricular Relaxation," *J Am Col Cardiol* 2003; 42(8):1463-70, proposed an index and a time interval that could be used to diagnose cardiac condition. The time interval is determined by the time of onset of mitral inflow or transmitral flow (from the left atrium to the left ventricle), $T_E$, and the time of onset of early diastolic velocity of the mitral annulus, $T_{Ea}$, wherein $T_{Ea}$ occurs generally after $T_E$.

Figure 4:
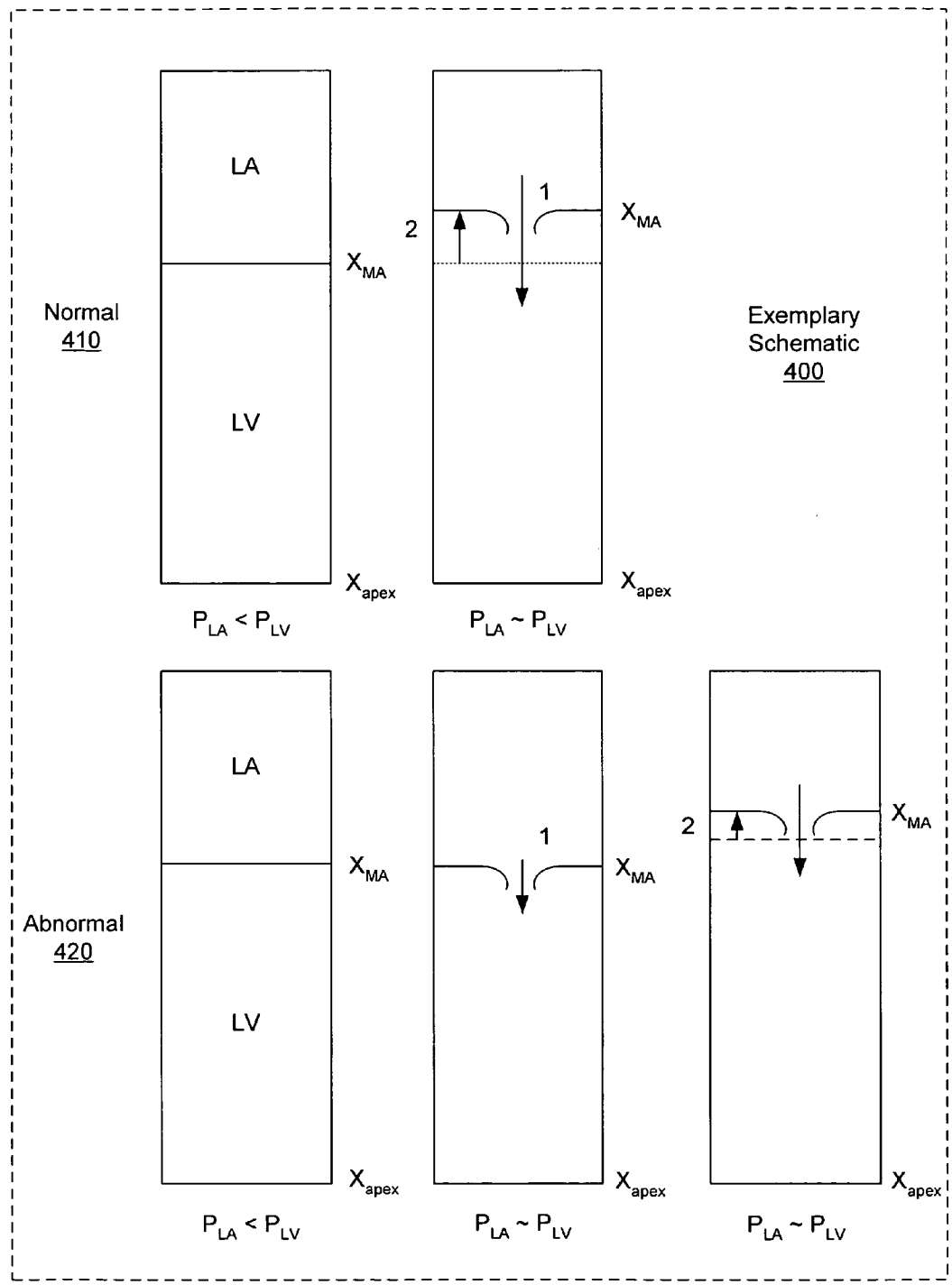
FIG. 4 is an exemplary schematic of normal cardiac condition and abnormal cardiac condition and associated mechanisms.

FIG. 4 shows a schematic 400 representative of normal cardiac condition 410 and abnormal cardiac condition 420. The schematic 400 aids in explanation of mechanisms associated with the times $T_E$ and $T_{Ea}$. For both cases 410, 420, at a time during late systole or early diastole, the pressure of the left ventricle exceeds the pressure of the left atrium; however, as time progresses, the pressure of the left ventricle falls as the pressure of the left atrium rises. When the pressures are approximately equal, a first mechanism (1) occurs wherein the mitral valve opens which may thereby allow for flow of blood from the left atrium to the left ventricle. For the normal cardiac condition 410, a second mechanism (2) occurs nearly synchronously with the first mechanism (1). The second mechanism (2) involves upward movement (cephalad) of the mitral annulus (MA), i.e., away from the apex of the left ventricle. In the schematic 400, $X_{MA}$ represents a position of the MA along the major axis of the left ventricle and $X_{apex}$ represents a position of the apex of the left ventricle. In the Rivas-Gotz et al. study, the $T_{Ea}$ and $T_E$ times were measured using Doppler flow and Doppler tissue techniques, respectively, with respect to peak R wave time. According to the study by Rivas-Gotz et al., the average time interval $T_{Ea}$-$T_E$ in normal humans is approximately 3 ms; thus, in the schematic 410, the first mechanism (1) occurs about 3 ms prior to the second mechanism (2).

The study by Rivas-Gotz et al. also provides data for humans with impaired ventricular relaxation as an abnormal group and a pseudonormal group. The average time interval for the abnormal group was about 33 ms and the average time interval for the pseudonormal group was about 37 ms. Thus, in these groups with impaired ventricular relaxation, a significant delay existed between $T_{Ea}$ and $T_E$ or onset of the first mechanism (1) and onset of the second mechanism (2). Therefore, the abnormal schematic 420 shows two separate events: onset of the first mechanism (1) and onset of the second mechanism (2). While the second mechanism includes an arrow representing flow, movement of the mitral annulus is generally opposite flow direction and hence flow through the open mitral valve increases in part due to movement of the mitral annulus.

The time intervals given by Rivas-Gotz et al. may be compared to those of Gibson and Francis. For example, Gibson and Francis noted an A2 to mitral opening interval of about 60 ms+/−20 ms and an A2 to onset of Doppler flow of about 85 ms+/−15 ms. While these data indicate that the time interval between mitral opening and Doppler flow is about 25 ms, Gibson and Francis also note that mitral cusp separation precedes the onset of flow on pulsed Doppler by about 10 ms to 12 ms in normal individuals and may extend up to 100 ms in patients with disease. Overall, these data indicate that the second mechanism (2) may be responsible for most of the flow from the left atrium to the left ventricle in early ventricular diastole. An exemplary method may determine that a cardiac condition exists if the time between mitral valve opening and onset of flow (or indicator thereof or ventricular motion related to flow) exceeds approximately 25 ms. In another exemplary method, a long-term average of such a difference may be used and compared to a short-term average using one or more criteria to determine if a cardiac condition exists, is improving or is worsening.

The Gibson and Francis study also discusses peak inward motion of the atrioventricular ring (AVR) and includes M mode echocardiographs that show, for normal individuals, peak inward motion approximately synchronous with heart sound A2. The study notes that the synchronous pattern of AVR motion is lost with left bundle branch block (e.g., peak inward motion occurring approximately 100 ms after A2). S2 or A2 or other indicator of aortic valve state may be used by an exemplary method, for example, in comparison to onset of flow (or indicator thereof or ventricular motion related to flow). In one example, a time difference between S2 or A2 and onset of flow (or indicator thereof or ventricular motion related to flow) in excess of approximately 100 ms may indicate a cardiac condition. In another exemplary method, a long-term average of such a difference may be used and compared to a short-term average using one or more criteria to determine if a cardiac condition exists, is improving or is worsening.

Various exemplary methods, devices, systems, etc., disclosed herein rely on direct and/or indirect measurements that indicate substantially asynchronous occurrence of mitral valve opening and upward movement of the mitral annulus. Various exemplary methods, devices, systems, etc., disclosed herein optionally rely on direct and/or indirect measurement of onset of upward movement of the mitral annulus with reference to one or more other events.

Figure 5:
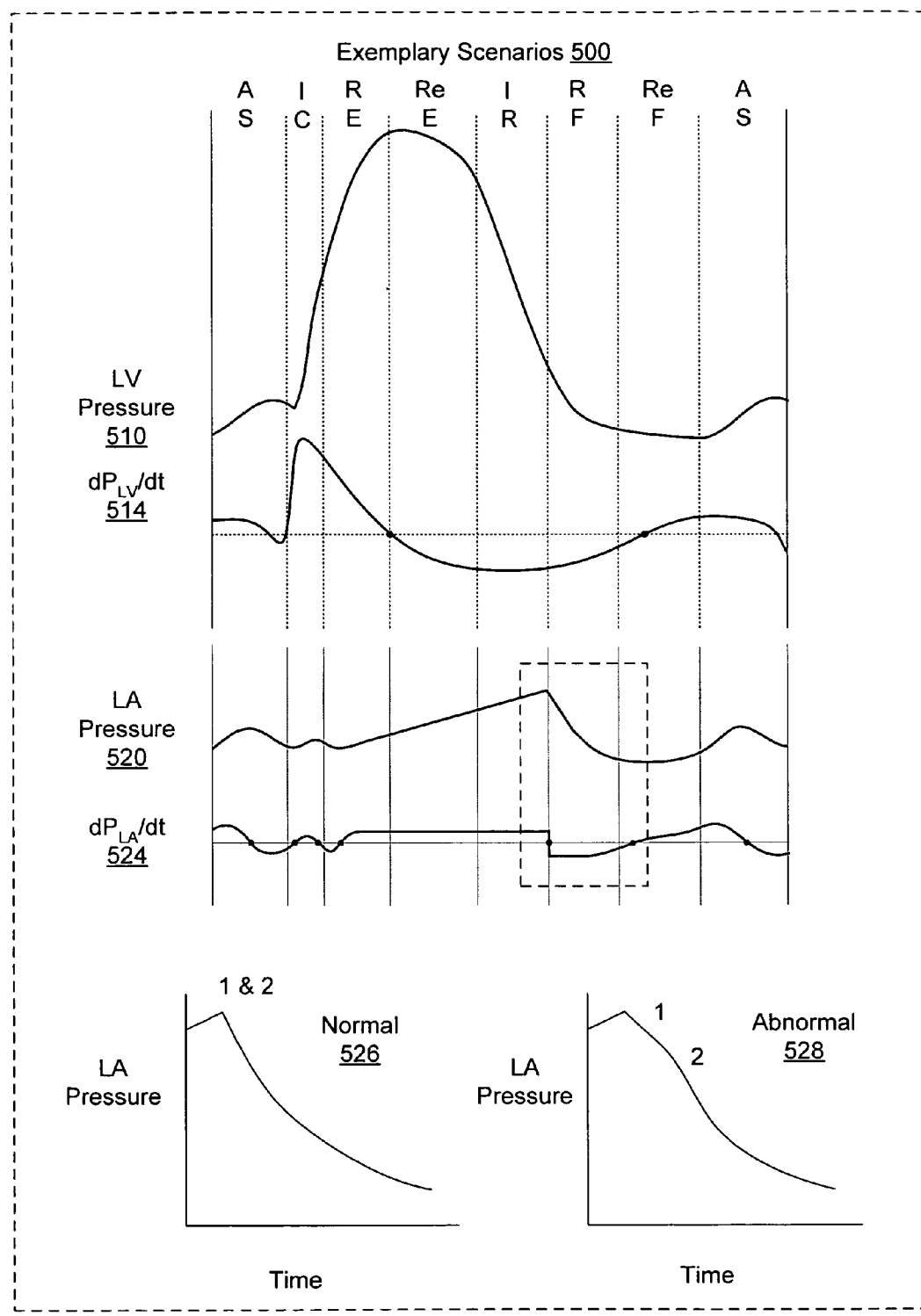
FIG. 5 is a diagram of exemplary scenarios associated with normal cardiac condition and abnormal cardiac condition with reference to left atrial pressure versus time.

FIG. 5 shows exemplary scenarios 500 that focus on variations in left atrial (LA) pressure with respect to time. A plot of LV pressure 510 and its first derivative with respect to time 514 versus time is presented for convenience. A plot of LA pressure 520 and its first derivative with respect to time 524 includes a dashed-line box around a region of interest that includes late ventricular systole and early ventricular diastole.

A plot 526 shows LA pressure versus time for normal cardiac condition. In this example, LA pressure decays in an exponential fashion with respect to time. The aforementioned first and second mechanisms (1 & 2), occur near simultaneously. In contrast, a plot 528 shows LA pressure versus time for abnormal cardiac condition wherein a change in rate of decay of LA pressure occurs in response to onset of the second mechanism (2), i.e., cephalad elongation of the left ventricle along its major axis. Consequently, direct or indirect measurement of LA pressure versus time during early ventricular diastole can provide information as to cardiac condition.

Various exemplary methods, devices, systems, etc., disclosed herein rely on direct and/or indirect measurement of left atrial pressure during early ventricular diastole to determine cardiac condition. The plot 524 of the first time derivative of left atrial pressure indicates that this parameter may be optionally used to determine cardiac condition. For example, a change in the rate of decreasing LA pressure may appear as an abrupt change in a first derivative. Other derivatives techniques and/or other mathematical techniques may be used.

Figure 6:
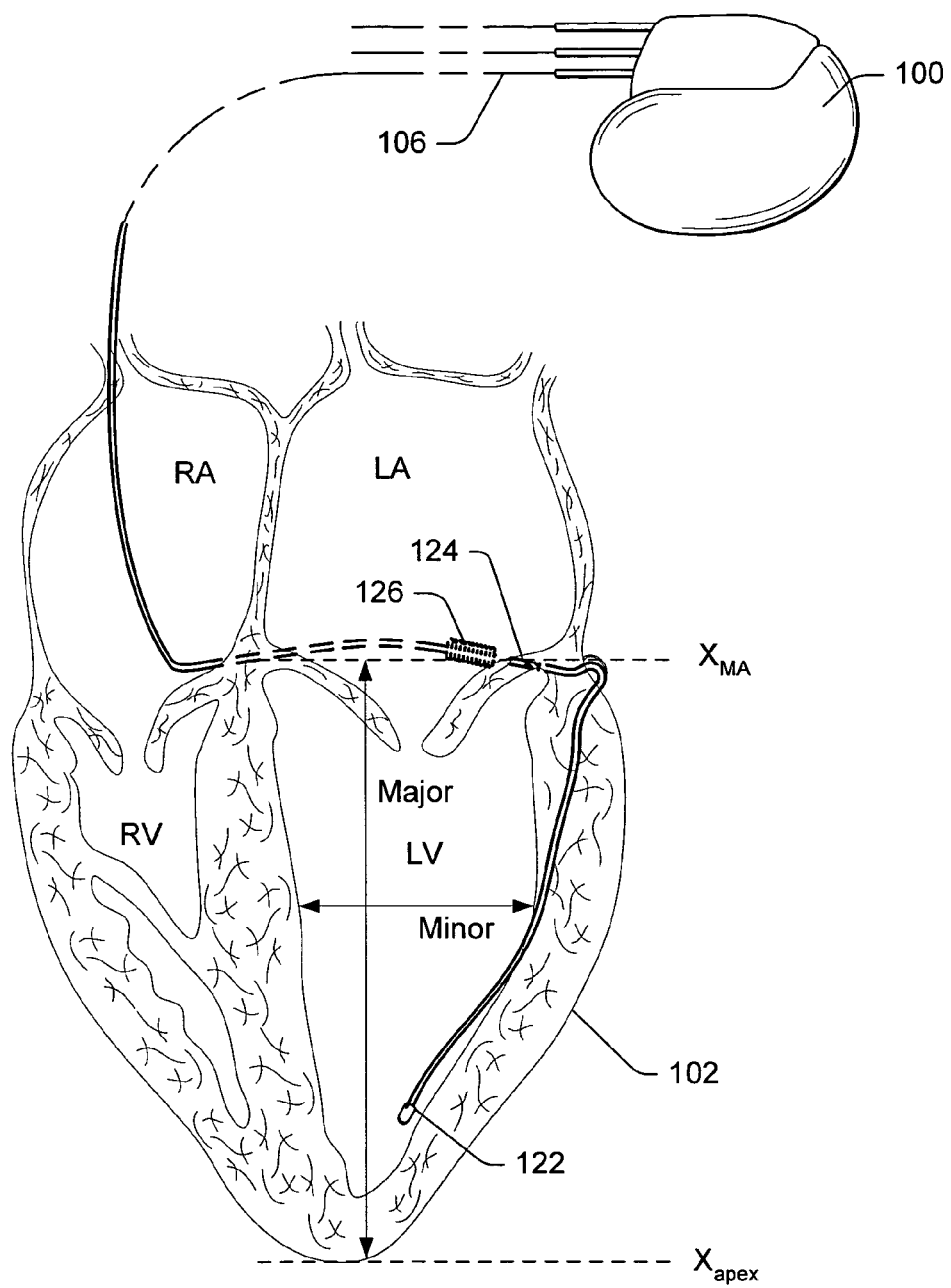
FIG. 6 is an approximate cross-sectional diagram of a heart, an exemplary implantable device and associated electrodes for use in measurements associated with cardiac motion during early ventricular diastole.

FIG. 6 shows an exemplary device 100 with a lead 106 as described with reference to FIGS. 1 and 2. The lead 106 includes one or more electrodes 122, 124, 126 positioned proximate to the left ventricle (LV) of the heart 102. In this example, the lead 106 passes from the right atrium (RA) through the ostium into the coronary sinus and into a tributary thereof. The electrodes 124, 126 are positioned on in the coronary sinus while the electrode 122 is positioned proximate to the apex of the left ventricle. The exemplary device 100 includes a case or other electrode proximate to the device 100. Accordingly, the exemplary device 100 is capable of measuring motion of the heart and in particular capable of direct and/or indirect measurement of upward (cephalad) motion of the mitral valve (e.g., mitral annulus or atrioventricular ring). In this example, upward motion corresponds to motion predominantly along the major axis of the left ventricle. The exemplary device 100 optionally measures onset of such upward motion during early diastole and optionally compares an onset time to one or more other event times. The exemplary device 100 optionally relies on such measurements to determine cardiac condition.

For example, the exemplary device 100 may sense an electrical signal, such as impedance, indicative of the position of the electrode 124 and/or 126 with respect to the electrode 122, a case electrode and/or other electrode. In particular, the electrodes 124, 126 in the coronary sinus do not depend heavily on changes in blood volume with respect to a current path to the exemplary device 100. Thus, a shortening of distance between such electrodes and the exemplary device 100 may correspond to upward motion of the mitral annulus during early ventricular diastole.

Various exemplary methods, devices, systems, etc., described herein optionally rely on direct and/or indirect distance and/or position measurements of the mitral annulus during early ventricular diastole. Such methods, devices, systems, etc., optionally rely on pressure measurements as well. Various exemplary methods rely on direct and/or indirect measurement upward motion with respect to one or more other events to determine cardiac condition.

Figure 7:
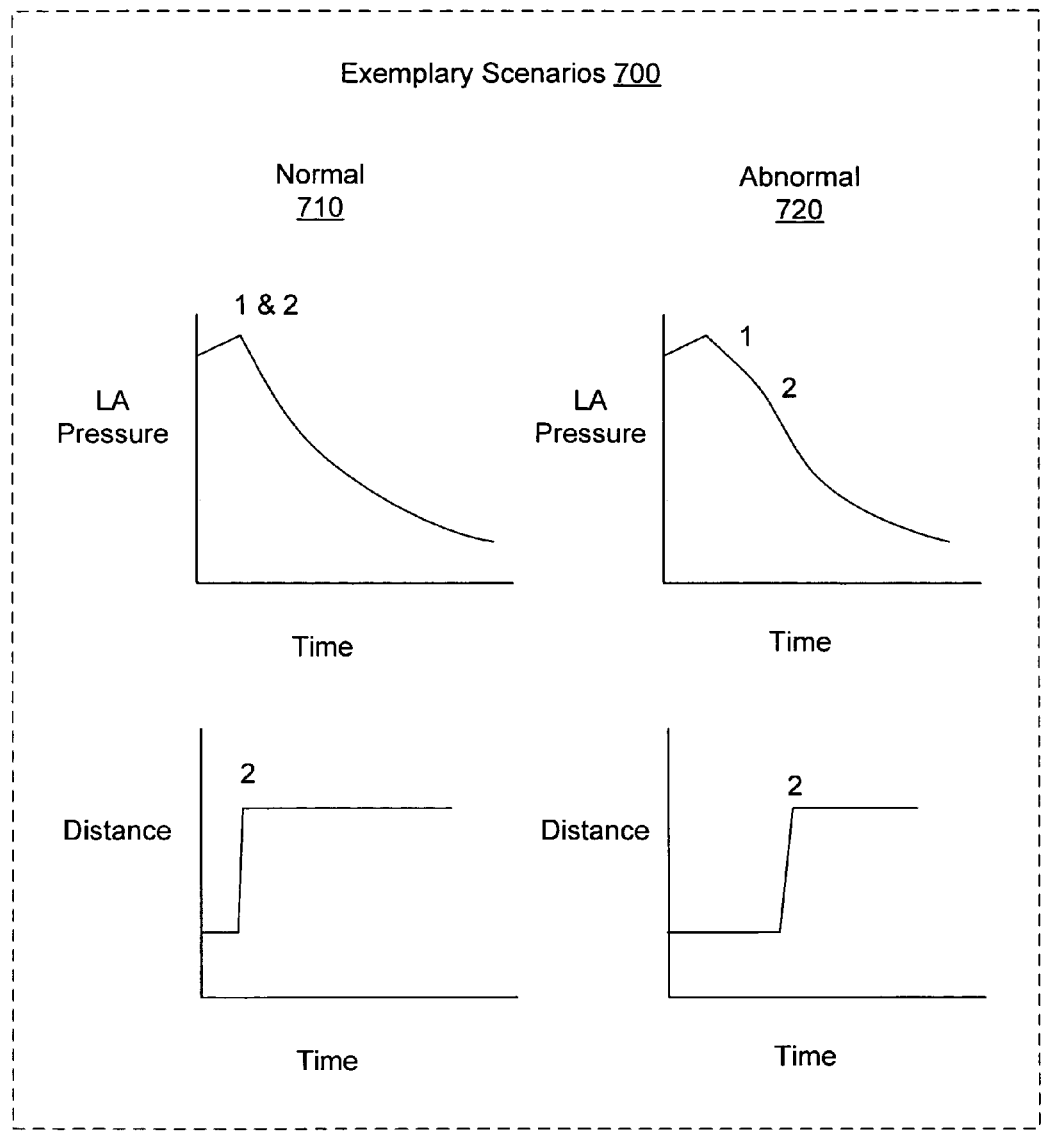
FIG. 7 is a diagram of exemplary scenarios associated with normal cardiac condition and abnormal cardiac condition with reference to left atrial pressure versus time and distance along a major axis of the left ventricle versus time.

FIG. 7 shows exemplary scenarios 700 for normal cardiac condition 710 and abnormal cardiac condition 720. The LA pressure versus time plots for the normal cardiac condition 710 and for abnormal cardiac condition 720 are as described above (see, e.g., plots 526, 528 of FIG. 5). Plots of distance versus time for normal cardiac condition and abnormal cardiac condition indicate onset of the second mechanism (2): onset of upward motion of the mitral annulus during early ventricular diastole.

The exemplary scenarios 700 illustrate use of motion information in conjunction with pressure information to determine cardiac condition. In particular, the exemplary scenarios 700 may pertain to determination of diastolic heart failure in patients that have substantially normal ejection fraction.

Figure 8:
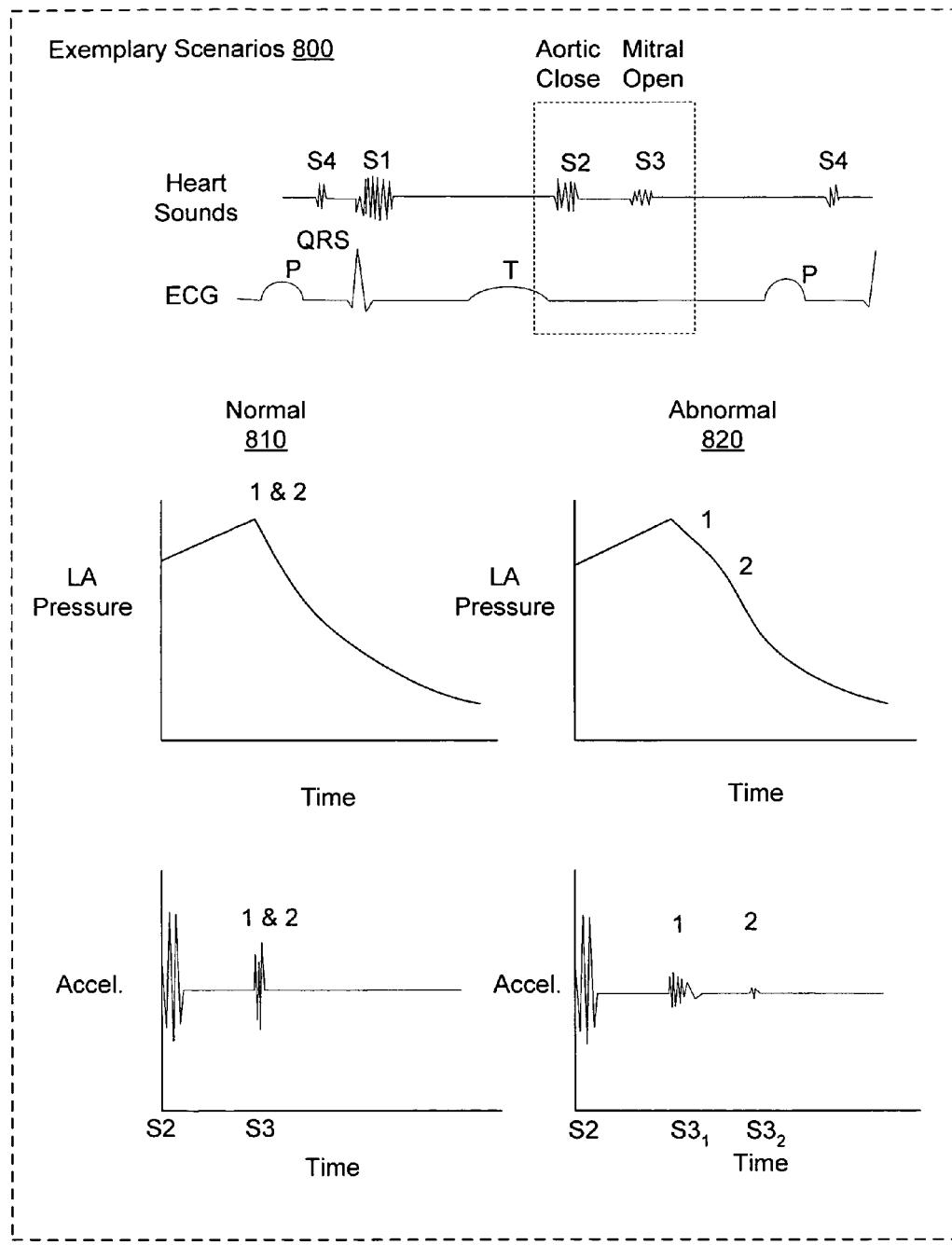
FIG. 8 is a diagram of exemplary scenarios associated with normal cardiac condition and abnormal cardiac condition with reference to left atrial pressure versus time and information associated with heart sounds versus time.

FIG. 8 shows exemplary scenarios 800 for normal cardiac condition 810 and abnormal cardiac condition 820. Plots of heart sounds and electrical activity of the heart versus time are shown for convenience (see, e.g., plot 300 of FIG. 3) along with a dashed-line box indicating a region of interest that includes late ventricular systole and early ventricular diastole. The LA pressure versus time plots for the normal cardiac condition 810 and for abnormal cardiac condition 820 are as described above (see, e.g., plots 526, 528 of FIG. 5). Plots of acceleration or phonocardiography versus time for normal cardiac condition and abnormal cardiac condition indicate a delayed onset of the second mechanism (2) for the abnormal cardiac condition scenario 820 (e.g., delayed onset of upward motion of the mitral annulus during early ventricular diastole); thus, for the S3 sound is broken into two components S3$_1$ and S3$_2$ or otherwise dispersed over time.

The exemplary scenarios 800 illustrate use of information associated with heart sounds in conjunction with pressure information to determine cardiac condition. In particular, the exemplary scenarios 800 may pertain to determination of diastolic heart failure in patients that have substantially normal ejection fraction. The exemplary scenarios 800 optionally rely on other information such as the aforementioned distance or motion information, for example, as it relates to the second mechanism.

An exemplary method may rely on sound, for example, through use of an accelerometer, to determine characteristics of heart sounds, such as, but not limited to, dispersion of the third heart sound (S3) (e.g., duration, etc.).

An exemplary method includes sensing information after closure of the aortic valve and prior to an atrial contraction of the subsequent cardiac cycle, the information representative of the state of the mitral valve and, based at least in part on the information, deciding whether a diastolic abnormality exists. Such an exemplary method optionally includes sensing left atrial pressure and/or sensing acceleration. Such sensing may sense the third heart sound and such an exemplary method may determine dispersion of the third heart sound over time, for example, where a dispersed third heart sound indicates that a diastolic abnormality exists.

Various exemplary methods, devices, systems, etc., optionally account for respiration. For example, respiratory sinus arrhythmia involves slowing of the sinus heart rate during an exhalation phase and a quickening of sinus heart rate during an inhalation phase. Accordingly, data acquisition during late ventricular systole and/or early ventricular diastole may occur based on respiratory phase. Such a data acquisition technique may act to reduce noise and provide a better determination of cardiac condition.

Figure 9:
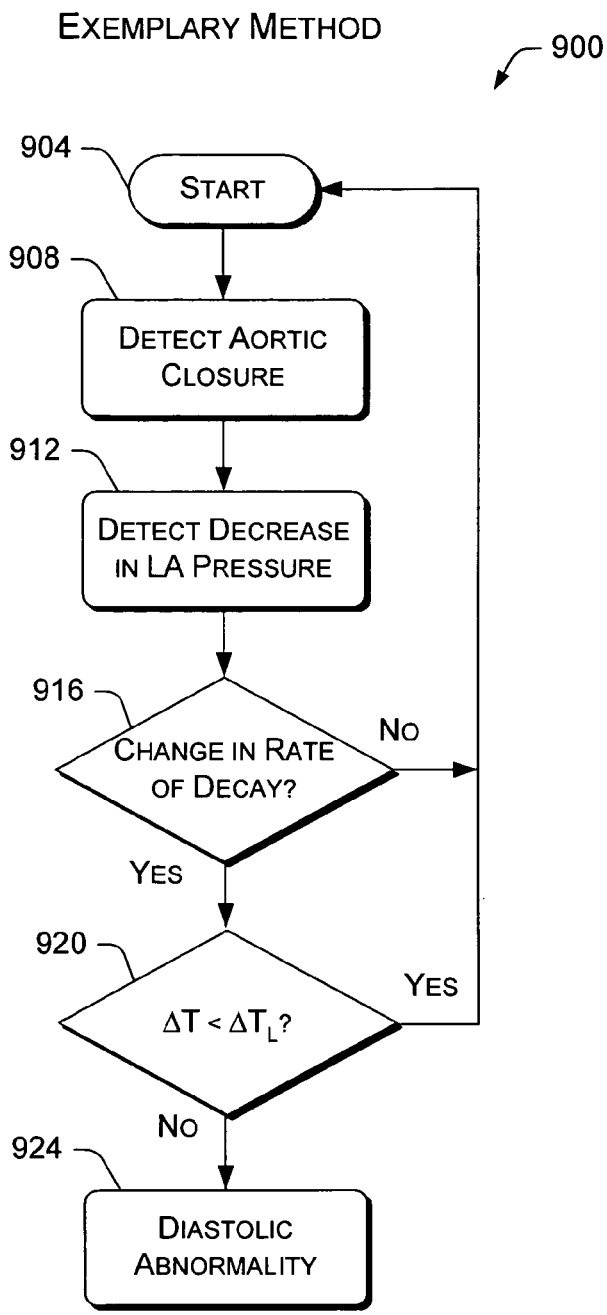
FIG. 9 is a block diagram of an exemplary method for determining whether a diastolic abnormality exists.

FIG. 9 shows a block diagram of an exemplary method 900 for determining whether a diastolic abnormality may exist. The method 900 commences in a start block 904, which optionally operates according to a schedule, an event, a command, etc. A detection block 908 detects closure of the aortic valve. The detection block 908 may rely on indirect and/or direct detection, for example, a pressure transducer, an accelerometer, or other sensor may sense information associated with status of the aortic valve. As shown in the plot 300 of FIG. 3, the left atrial pressure has a positive slope with respect to time at the time of the aortic valve closure; however, sometime thereafter, the slope generally changes to a negative slope. Another detection block 912 acts to detect a decrease in the left atrial pressure and/or a change in slope from positive to negative of the left atrial pressure with respect to time. Such a decrease or change typically indicates that the mitral valve between the left atrium and the left ventricle has opened; thereby allowing for equalization of pressure between these two chambers, which may include a flow of blood from the left atrium to the left ventricle (e.g., early ventricular diastole).

Once a change in left atrial pressure occurs, the exemplary method 900 then acquires left atrial pressure information for a period, for example, of about 50 ms. A decision block 916 follows that decides whether a change in the rate of decay of the left atrial pressure occurred during the period (e.g., based on an analysis of the acquired information). If no change occurred, then the method continues at the start block 904. However, if a change in the rate of decay occurred, then the method continues in another decision block 920. The decision block 920 compares the time of the change in the rate of decay ($\Delta T$) to a time limit ($\Delta T_L$). If the time $\Delta T$ is less than the limit $\Delta T_L$, a favorable comparison, then the method 900 continues at the start block 904. However, an unfavorable comparison causes the method 900 to continue in a diagnosis block 924 wherein the patient is diagnosed as having a condition indicative of a diastolic abnormality. While in this example, the time may depend on the detection of a decrease in left atrial pressure, the time of aortic valve closure may be used as an alternative or in addition to the detection of a decrease in left atrial pressure.

According to the exemplary method 900, a change in the rate of decay after about 25 ms from opening of the mitral valve may indicate that the first mechanism and the second mechanism did not occur within a "normal" time period (e.g., ~5 ms). Consequently, incoordinate relaxation of the left ventricle may have occurred indicative of diastolic abnormality. In this example, the nature of the change may not be required as it serves to mark the onset of the second mechanism, which can act to alter the left atrial pressure versus time curve.

While the exemplary method 900 includes a time period for acquisition of left atrial pressure information after opening of the mitral valve and a time limit, such an exemplary method optionally includes only a time period for acquisition or only a time limit to make determinations pertaining to diastolic abnormalities. For example, if no change in the rate of decay occurs during the acquisition time indicative of a separation between the first and second mechanisms, then diastolic condition may be deemed normal. In another example, acquisition of left atrial pressure information occurs throughout a cardiac cycle and information pertaining to early ventricular diastole is analyzed and compared to a time limit to determine if a separation between the first and second mechanisms exists indicative of a diastolic abnormality.

Figure 10:
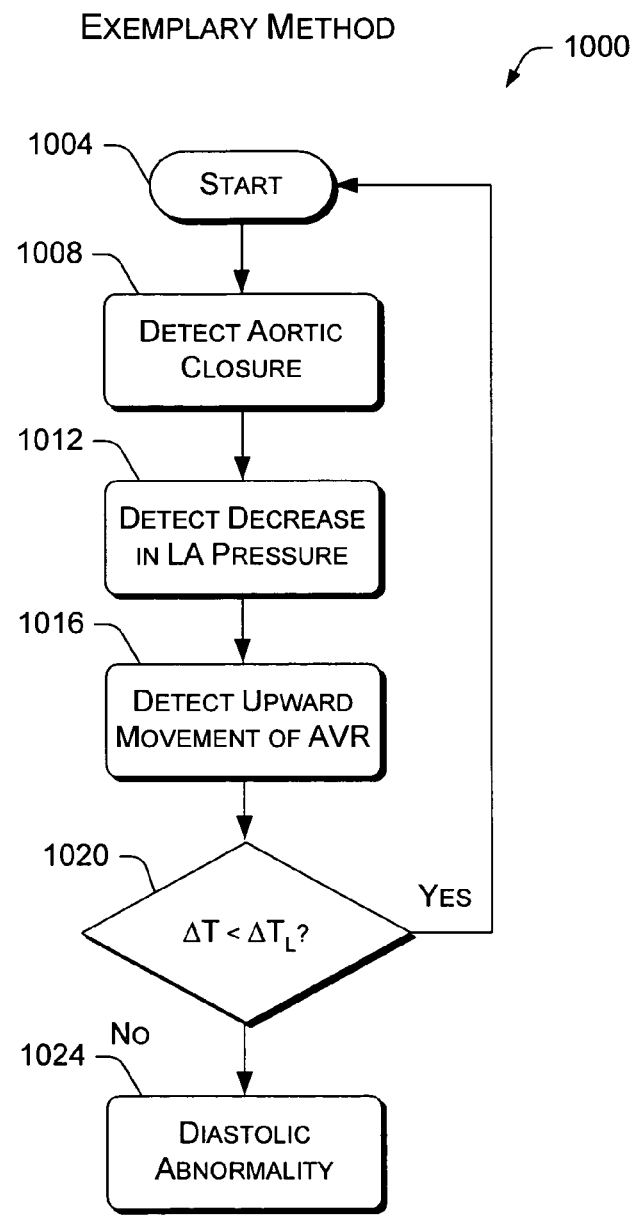
FIG. 10 is a block diagram of an exemplary method for determining whether a diastolic abnormality exists.

FIG. 10 shows a block diagram of an exemplary method 1000 for determining whether a diastolic abnormality may exist. The method 1000 commences in a start block 1004, which optionally operates according to a schedule, an event, a command, etc. A detection block 1008 detects closure of the aortic valve. The detection block 1008 may rely on indirect and/or direct detection, for example, a pressure transducer, an accelerometer, or other sensor may sense information associated with status of the aortic valve. As shown in the plot 300 of FIG. 3, the left ventricular pressure has a positive slope with respect to time at the time of the aortic valve closure; however, sometime thereafter, the slope changes to a negative slope. Another detection block 1012 acts to detect a decrease in the left atrial pressure and/or a change in slope from positive to negative of the left atrial pressure with respect to time. Such a decrease or change typically indicates that the mitral valve between the left atrium and the left ventricle has opened; thereby allowing for equalization of pressure between these two chambers, which may include a flow of blood from the left atrium to the left ventricle (e.g., early ventricular diastole). The detection block 1012 may note the timing of the detection.

Another detection block 1016 acts to detect upward movement of the atrioventricular ring (AVR) or mitral annulus (MA). A decision block 1020 compares a time difference $\Delta T$ between the detection of decrease in the left atrial pressure, the detection of upward movement of the AVR and/or the detection of aortic valve closure to a time difference limit $\Delta T_L$. If the time difference $\Delta T$ exceeds the limit $\Delta T_L$, then the method 1000 continues at a diagnosis block 1024 that indicates a condition associated with diastolic abnormality. Various times are indicated above and may be used in selecting an appropriate limit. Such a limit is optionally adjustable based on patient condition or patient history.

Figure 11:
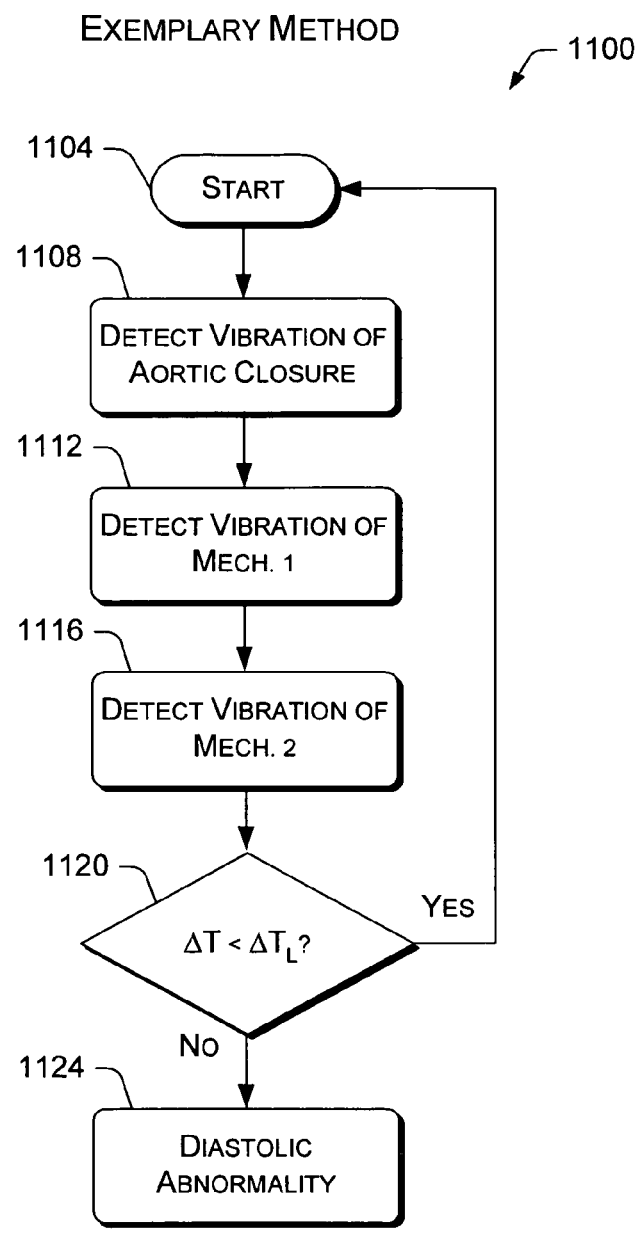
FIG. 11 is a block diagram of an exemplary method for determining whether a diastolic abnormality exists.

FIG. 11 shows a block diagram of an exemplary method 1100 for determining whether a diastolic abnormality may exist. The method 1100 commences in a start block 1104, which optionally operates according to a schedule, an event, a command, etc. A detection block 1108 detects closure of the aortic valve. The detection block 1108 relies on an accelerometer to detect vibrations associated with closure of the aortic valve. As shown in the plot 300 of FIG. 3, the left ventricular pressure has a positive slope with respect to time at the time of the aortic valve closure; however, sometime thereafter, the slope changes to a negative slope. Another detection block 1112 acts to detect opening of the mitral valve between the left atrium and the left ventricle, which may include a flow of blood from the left atrium to the left ventricle (e.g., early ventricular diastole). The detection block 1112 may note the timing of the detection.

Another detection block 1116 acts to detect vibrations associated with upward movement of the atrioventricular ring (AVR) or mitral annulus (MA) using an accelerometer. A decision block 1120 compares a time difference $\Delta T$ between the detection of mitral valve opening, the detection of upward movement of the AVR and/or the detection of aortic valve closure to a time difference limit $\Delta T_L$. If the time difference $\Delta T$ exceeds the limit $\Delta T_L$, then the method 1100 continues at a diagnosis block 1124 that indicates a condition associated with diastolic abnormality. Various times are indicated above and may be used in selecting an appropriate limit. Such a limit is optionally adjustable based on patient condition or patient history.

The exemplary methods 900, 1000, 1100 optionally rely on detecting a change in state of a cardiac valve (e.g., aortic valve and/or mitral valve), detecting elongation of the left ventricle substantially along its major axis, determining a time difference between the change in state of the cardiac valve and the elongation of the left ventricle; and, based at least in part on the time difference, deciding whether a diastolic abnormality exists.

Figure 12:
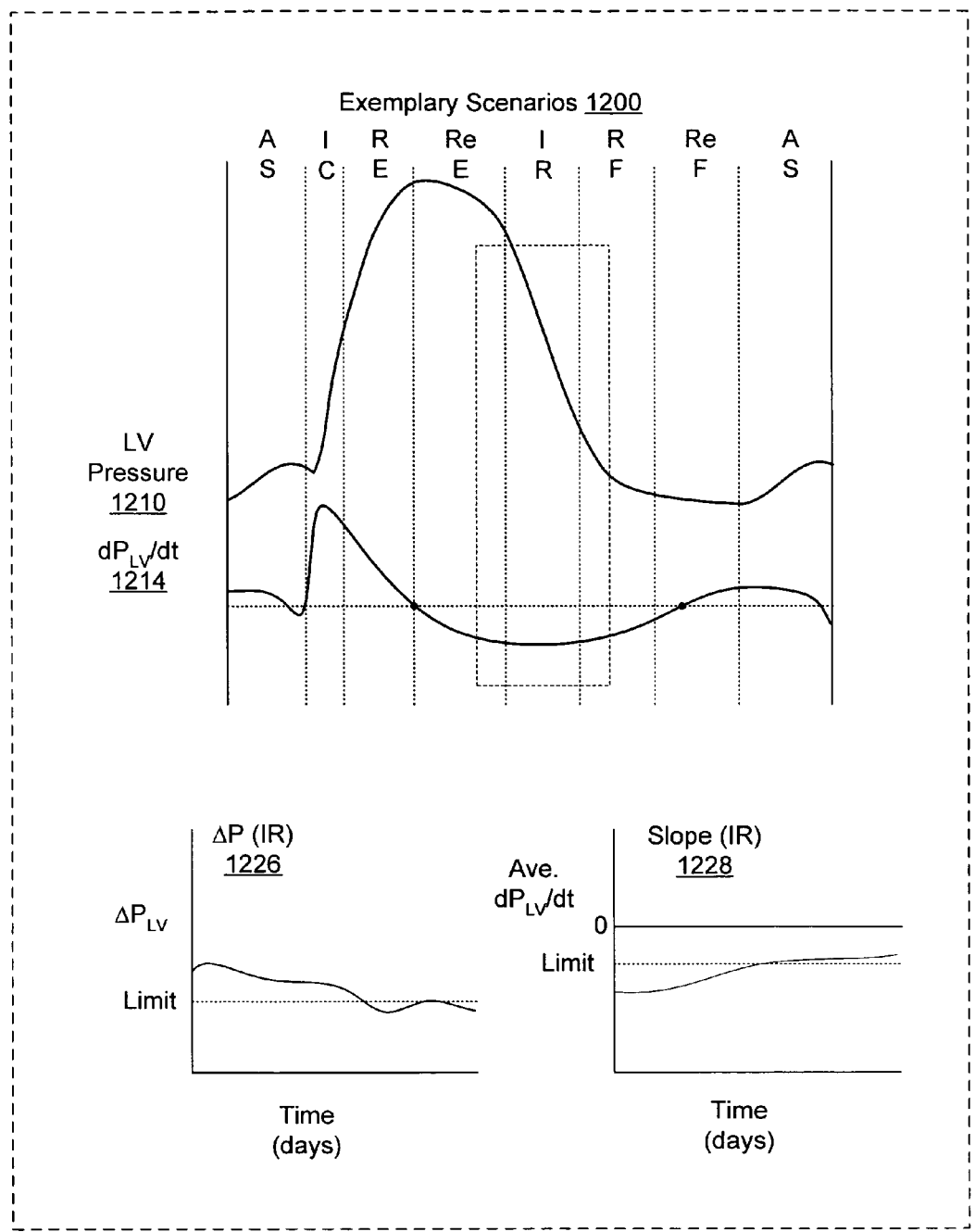
FIG. 12 is a diagram of exemplary scenarios associated with normal cardiac condition and abnormal cardiac condition with reference to left ventricular pressure versus time.

As mentioned above, Gibson and Francis stated that IVRT may be used an indicator of disease. FIG. 12 shows various exemplary scenarios 1200 whereby an implantable device may use pressure information and optionally other information to assess cardiac condition.

A plot of LV pressure 1210 and its first derivative with respect to time 1214 versus time is presented for convenience where a dashed-line box around a region of interest that includes at least part of the isovolumetric relaxation phase (IR). A plot 1226 shows change in left ventricular pressure ($\Delta P_{LV}$), for example, measured between two points in time in or around the IR cardiac phase, versus time in days where a limit may be used to help indicate a disease state or worsening of cardiac condition. As shown, $\Delta P_{LV}$ decreases over days to fall below a limit, which may cause an implantable device to issue an alert or record an event.

A plot 1228 shows the time derivative of the left ventricular pressure versus time in days. The time derivative may be determined based on a set time period, two times optionally related to cardiac events, or on set pressures reasonably expected to occur during or near the IR cardiac phase. Such exemplary methods for determining a slope (i.e., time derivative of left ventricular pressure) may be used to indicate a disease state or worsening of cardiac condition. As shown in the plot 1228, a negative slope below a limit may indicate normal cardiac condition while a negative slope that exceeds the limit may indicate an abnormal cardiac condition (e.g., a disease state, etc.).

Various exemplary methods, devices, systems, etc., disclosed herein rely on direct and/or indirect measurement of left ventricular pressure at least partially during an isovolumetric relaxation (IR) phase of the heart to determine cardiac condition. The plot 1214 of the first time derivative of left ventricular pressure indicates that this parameter may be optionally used to determine cardiac condition. Other derivatives techniques and/or other mathematical techniques may be used to analyze a left ventricular pressure; alternatively, or in addition to, a sensor may measure slope of left ventricular pressure directly. Models may optionally be used to determine one or more factors that reflect changes in left ventricular pressure with respect to time at least partially during an isovolumetric relaxation (IR) phase.

Various exemplary methods, devices, systems, etc., may rely on one or more of the techniques described in FIGS. 5-12. For example, an exemplary method may rely on left atrial pressure and left ventricular pressure information to determine cardiac condition. In another example, an exemplary method may rely on "axis" information from an impedance or other measurement and pressure information. In yet another example, an exemplary method may rely on "sound" information and optionally axis or pressure information.

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method, implemented by an implantable device, the method comprising:
   detecting a change in state of a cardiac valve wherein a state of a cardiac valve comprises a closed state or an open state;
   detecting elongation of the left ventricle substantially along its major axis due to relaxation of the left ventricle;
   determining a time difference between the change in state of the cardiac valve and the elongation of the left ventricle;
   comparing the time difference between the change in state of the cardiac valve and the elongation of the left ventricle to a threshold; and
   based at least in part on the comparison, deciding whether a diastolic abnormality exists.

2. The method of claim 1 wherein the change in state of a cardiac valve corresponds to a change in state of the mitral valve.

3. The method of claim 1 wherein the change in state of a cardiac valve corresponds to a change in state of the aortic valve.

4. The method of claim 1 wherein the detecting a change in state comprises sensing pressure using an implantable pressure sensor.

5. The method of claim 1 wherein the detecting a change in state comprises sensing vibration using an implantable vibration sensor.

6. The method of claim 1 wherein the detecting elongation comprises sensing impedance using an implantable impedance sensor.

* * * * *